(12) United States Patent
Brendel et al.

(10) Patent No.: US 8,179,658 B2
(45) Date of Patent: May 15, 2012

(54) ELECTROMAGNETIC INTERFERENCE FILTER AND METHOD FOR ATTACHING A LEAD AND/OR A FERRULE TO CAPACITOR ELECTRODES

(75) Inventors: Richard L. Brendel, Carson City, NV (US); Robert A. Stevenson, Canyon Country, CA (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 293 days.

(21) Appl. No.: 12/563,919

(22) Filed: Sep. 21, 2009

(65) Prior Publication Data

US 2010/0134951 A1 Jun. 3, 2010

Related U.S. Application Data

(63) Continuation-in-part of application No. 12/437,345, filed on May 7, 2009, and a continuation-in-part of application No. 12/269,255, filed on Nov. 12, 2008, now Pat. No. 7,917,219.

(51) Int. Cl.
*H01G 4/35* (2006.01)

(52) U.S. Cl. ..... 361/302; 361/303; 361/305; 361/301.2; 361/321.2; 361/308.1; 333/183; 333/185

(58) Field of Classification Search ............. 361/302, 361/303, 305, 308.1; 333/182, 185
See application file for complete search history.

(56) References Cited

U.S. PATENT DOCUMENTS

| | | | |
|---|---|---|---|
| 4,424,551 A | 1/1984 | Stevenson et al. | |
| 5,333,095 A | 7/1994 | Stevenson et al. | |
| 5,870,272 A * | 2/1999 | Seifried et al. | 361/302 |
| 6,031,710 A * | 2/2000 | Wolf et al. | 361/302 |
| 6,566,978 B2 | 5/2003 | Stevenson et al. | |
| 6,619,763 B2 * | 9/2003 | Trinh et al. | 361/302 |
| 6,643,903 B2 | 11/2003 | Stevenson et al. | |
| 6,765,779 B2 | 7/2004 | Stevenson et al. | |
| 6,999,818 B2 | 2/2006 | Stevenson et al. | |
| 7,038,900 B2 * | 5/2006 | Stevenson et al. | 361/302 |
| 2009/0116167 A1 | 5/2009 | Stevenson et al. | |
| 2009/0288280 A1 * | 11/2009 | Brendel et al. | 29/25.41 |

* cited by examiner

*Primary Examiner* — Nguyen T Ha
(74) *Attorney, Agent, or Firm* — Kelly & Kelley, LLP (57) ABSTRACT

A discoidal feedthrough capacitor has its active electrode plates disposed within a dielectric body so that an edge of the active electrode plates is exposed at a surface of a through-hole for a conductive lead. The conductive lead is conductively coupled to the exposed edge of the electrode plates without an intervening conductive termination surface. Similarly, a ground electrode plate set of the feedthrough capacitor may have an edge exposed at the outer periphery of the capacitor for conductively coupling the exposed edge of the ground electrode plate to a conductive ferrule without an intervening conductive termination surface.

22 Claims, 9 Drawing Sheets

BODY FLUID SIDE

BODY FLUID SIDE

FIG. 10  BODY FLUID SIDE

FIG. 11  BODY FLUID SIDE

ELECTROMAGNETIC INTERFERENCE FILTER AND METHOD FOR ATTACHING A LEAD AND/OR A FERRULE TO CAPACITOR ELECTRODES

BACKGROUND OF THE INVENTION

This invention relates generally to EMI filter terminal subassemblies and related methods of construction, particularly of the type used in active implantable medical devices (AIMDs) such as cardiac pacemakers, implantable defibrillators, cochlear implants, neurostimulators, active drug pumps and the like, which are designed to decouple and shield undesirable electromagnetic interference (EMI) signals from an associated device. More particularly, the present invention relates to an improved EMI filter terminal assembly and methods for directly attaching the electrode plates of a feedthrough capacitor to the associated lead wires and/or ferrule.

Feedthrough terminal assemblies are generally well known for connecting electrical signals through the housing or case of an electronic instrument. For example, in implantable medical devices, the terminal pin assembly comprises one or more conductive terminal pins supported by an insulator structure for feedthrough passage from the exterior (body fluid side) to the interior of the medical device. Many different insulator structures and related mounting methods are known for use in medical devices wherein the insulator structure provides a hermetic seal to prevent entry of body fluids into the housing of the medical device. In a cardiac pacemaker, for example, the feedthrough terminal pins are typically connected to one or more lead wires within the case to conduct pacing pulses to cardiac tissue and/or detect or sense cardiac rhythms. However, the lead wires can also undesirably act as an antenna and thus tend to collect stray electromagnetic interference (EMI) signals for transmission into the interior of the medical device. Studies conducted by the United States Food and Drug Administration (FDA), Mount Sinai Medical Center and other researchers have demonstrated that stray EMI, such as radio frequency (RF) signals produced by cellular telephones, can seriously disrupt the proper operation of the pacemaker. It has been well documented that pacemaker inhibition, asynchronous pacing and misbeats can all occur. All of these situations can be dangerous or even life threatening for a pacemaker-dependent patient.

In prior art devices, such as those as shown in U.S. Pat. Nos. 5,333,095 and 4,424,551, the contents of which are incorporated herein, the hermetic terminal pin subassembly has been combined in various ways with a feedthrough capacitor filter to decouple EMI signals to the equipotential housing of the medical device. As described in U.S. Pat. No. 6,999,818 (the contents of which are incorporated herein), the feedthrough capacitor can also be combined with inductor elements thereby forming what is known in the art as a multi-element low pass filter.

In general, the feedthrough capacitor, which has one or more passages or feedthrough holes, is connected to the hermetic terminal of the implantable medical device in a variety of ways. In order for the EMI filtered feedthrough capacitor to properly operate, a low impedance and low resistance electrical connection must be made between the capacitor ground electrode plate stack and the metallic ferrule of the hermetic seal, which in turn mechanically and electrically connects to the overall conductive housing of the implantable medical device. For example, in a cardiac pacemaker, the hermetic terminal assembly consists of a conductive ferrule generally made of titanium which is laser welded to the overall titanium housing of the implantable medical device. This not only provides a hermetic seal, but also makes the ferrule of the hermetic terminal a continuous part of the overall electromagnetic shield that protects the electronics of the implantable medical device from EMI. The feedthrough capacitor is in turn electrically and mechanically bonded to the ferrule of said hermetic terminal.

In the past, and in particular as described in U.S. Pat. Nos. 5,333,095 and 4,424,551, the connection between the feedthrough capacitor and the ferrule is typically performed using a thermal-setting conductive adhesive. One such material is a silver-flake or sphere loaded conductive polyimide. The connection between the lead wires of the hermetic terminal and the passages or feedthrough holes of the ceramic feedthrough capacitor are typically made with solder, a thermal-setting conductive adhesive, a braze material or the like. The perimeter or diameter of the feedthrough capacitor is typically where its ground electrodes are connected (reference U.S. Pat. No. 5,333,095). Methods for holding the thermal-setting conductive material in place are well described in the prior art. See, for example, U.S. Pat. No. 6,643,903, which describes a capture flange for convenient dispensing of materials. Various methods for providing for leak detection are also provided as described in U.S. Pat. No. 6,566,978.

Feedthrough capacitors generally have a metallization or termination surface around their outside diameter or outside perimeter. This places all of the ground electrode plates in parallel and also provides for a convenient place for attachment of solder or thermal-setting conductive adhesives or the like. In a similar fashion, the inside passages or feedthrough holes also have an inside diameter metallization surface which connects the active electrode plate set together in parallel. Various methods are known for making an electrical contact between the feedthrough lead wire and this inside diameter metallization which in turn contacts all of the electrode plates of the active electrode plate set.

Application of the prior art metallization (also known as termination) on the capacitor outside diameter and also into all of the capacitor feedthrough holes is a time consuming and costly process. For a typical round quadpolar ceramic feedthrough capacitor, application of the termination usually involves placing the capacitor on a mandrel and then rolling its outside diameter through a bed of a liquid silver-bearing glass frit. This glass frit is fired in place thereby conductively coupling all of the ground electrode plates in parallel. Then a vacuum pull process is used to pull metallization or termination material consisting of the same silver or palladium silver-bearing glass frit through the inside passages or feedthrough holes. This is followed by another high temperature glass firing operation. These operations are then followed by lapping or clean up operations to be sure that there is no metallization left on the top or bottom surfaces that could lead to shorting out of the device. Termination paste dipping for rectangular parts or electroplating is an alternative process to accomplish the above. While these processes tend to be very reliable, they are very expensive and time consuming.

One such methodology is described in U.S. Pat. No. 4,424,551. However, the process of injecting a material through repeated centrifuge steps and then repeated microblast cleaning steps is very time consuming, costly, and tends to result in low process yields. A superior method of mounting the ceramic feedthrough capacitor is described in U.S. Pat. No. 5,333,095 wherein the capacitor is surface mounted. This has great advantages in that the ceramic capacitor itself is not subjected to undue mechanical or thermal stresses during laser weld installation of the hermetic seal subassembly and to the overall housing of the AIMD. It is relatively easy to make the perimeter or outside diameter ground attachment to the ferrule. However, for a capacitor with a flat surface with lead wires extending through its inside passageways or through-holes, it is problematic to make a reliable electrical connection. This is because solders, thermal-setting conductive polymers, brazes and the like tend to sit up on top of the capacitor. During re-flow operations, at high temperature these materials tend to migrate into undesirable positions. Sometimes the materials will migrate together and even short out one lead to another.

Accordingly, there is a need for an improved EMI filter terminal assembly and methods for making connections between a feedthrough capacitor and its associated lead wires and/or ferrule, which overcome the aforementioned difficulties. The present invention solves all the aforementioned problems and provides other related advantages.

SUMMARY OF THE INVENTION

The present invention resides in an electromagnetic interference (EMI) filter comprising (1) a capacitor comprised of a dielectric body having first and second sets of electrode plates disposed therein, at least one of the first and second sets of electrode plates having an edge exposed at a surface of the dielectric body, and (2) a conductive lead and/or a conductive ferrule disposed adjacent to the exposed edge of the electrode plates and conductively coupled to the exposed edge of the electrode plates without an intervening conductive termination surface.

The capacitor may comprise a feedthrough capacitor having at least one through-hole in which at least a portion of the conductive lead is disposed, and an outer-periphery adjacent, at least in part, to the conductive ferrule. The first set of electrode plates has an edge exposed at an inner surface of the through-hole, and the conductive lead is conductively coupled to the exposed edge of the first set of electrode plates without an intervening conductive termination surface fixed to the inner surface of the through-hole over the exposed edge of the first set of electrode plates. The second set of electrode plates has an edge exposed at the outer periphery of the capacitor, and the conductive ferrule is conductively coupled to the exposed edge of the second set of electrode plates without an intervening conductive termination surface fixed to the outer periphery of the capacitor over the exposed edge of the second set of electrode plates.

An electrically conductive material may be disposed between the conductive lead or ferrule and the adjacent exposed edge of the electrode plates, for conductively coupling the conductive lead or ferrule to the adjacent exposed edge of the electrode plates. The exposed edge of the electrode plates may be formed to extend outwardly from the surface of the dielectric body. This is accomplished by controlling shrinkage of the dielectric body of the capacitor to be greater than shrinkage of the electrode plates during manufacture of the capacitor. Moreover, the surface of the dielectric body of the capacitor may comprise an acid-etched surface.

In several illustrated embodiments, the conductive lead or ferrule may directly contact the exposed edge of the electrode plates. Further, a surface of the conductive lead or ferrule may comprise a knurled, sputtered, threaded or roughened surface.

The electrically conductive material may comprise an adhesive or a thermal-setting material. More particularly, the adhesive may comprise a thermal-setting adhesive comprising a polymer selected from the group consisting of: epoxies, polyimides, polyethylene oxide, polyurethane, silicone, polyesters, polycarbonate, polyethylene, polyvinyl chloride, polypropylene, methylacrylate, para-xylylene, and polypyrrhol. Alternatively, the adhesive may include a biocompatible filler such as a noble metal filler, or a non-migratable and biocompatible conductive filler selected from the group consisting of: titanium, platinum and platinum/iridium alloys, tantalum, niobium, zirconium, hafnium, nitinol, Co—Cr—Ni alloys such as MP35N, Havar® and Elgiloy®, stainless steel, gold, ZrC, ZrN, TiN, NbO, TiC, TaC, Indium Oxide/Indium Tin Oxide.

In some embodiments, it is preferred that the capacitor and the conductive lead or ferrule comprise bio-compatible and non-migratable materials suitable for prolonged direct body fluid exposure.

In a related process of manufacturing an electromagnetic interference (EMI) filter, the invention comprises the steps of (1) providing a capacitor comprised of a dielectric body having first and second sets of electrode plates therein, at least one of the first and second sets of electrode plates having an edge exposed at a surface of the dielectric body, (2) placing a conductive lead or ferrule adjacent to the exposed edge of the electrode plates, and (3) conductively coupling the exposed edge of the electrode plates directly to the conductive lead or ferrule without an intervening conductive termination surface.

More specifically, the inventive process includes the steps of (1) providing a capacitor comprised of a dielectric material having active and ground electrode plates therein, and at least one through-hole, (2) forming a well in a surface of the capacitor at one end of the through-hole, (3) inserting a pin or a lead wire at least partially into the through-hole, (4) placing an electrically conductive material in the well, wherein the electrically conductive material comprises a liquid or semi-liquid material during at least a portion of the manufacturing process, and (5) utilizing the electrically conductive material to conductively couple the pin or the lead wire to one of the active or ground electrode plates.

The electrically conductive material may conductively couple the lead or lead wire to one of the active or ground electrode plates directly and without an intervening conductive termination surface for the electrode plates. As mentioned above, shrinkage of the dielectric material of the capacitor may be greater than shrinkage of the electrode plates such that an end of the electrode plates conductively coupled to the electrically conductive material, extends inwardly from the dielectric material into the through-hole.

The process may include the step of acid-etching the dielectric material adjoining the through-hole prior to the step of conductively coupling the pin or the lead wire to one of the active or ground electrode plate sets.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

In the description that follows, functionally equivalent components generally have the same reference numbers throughout the drawings.

Figure 1:
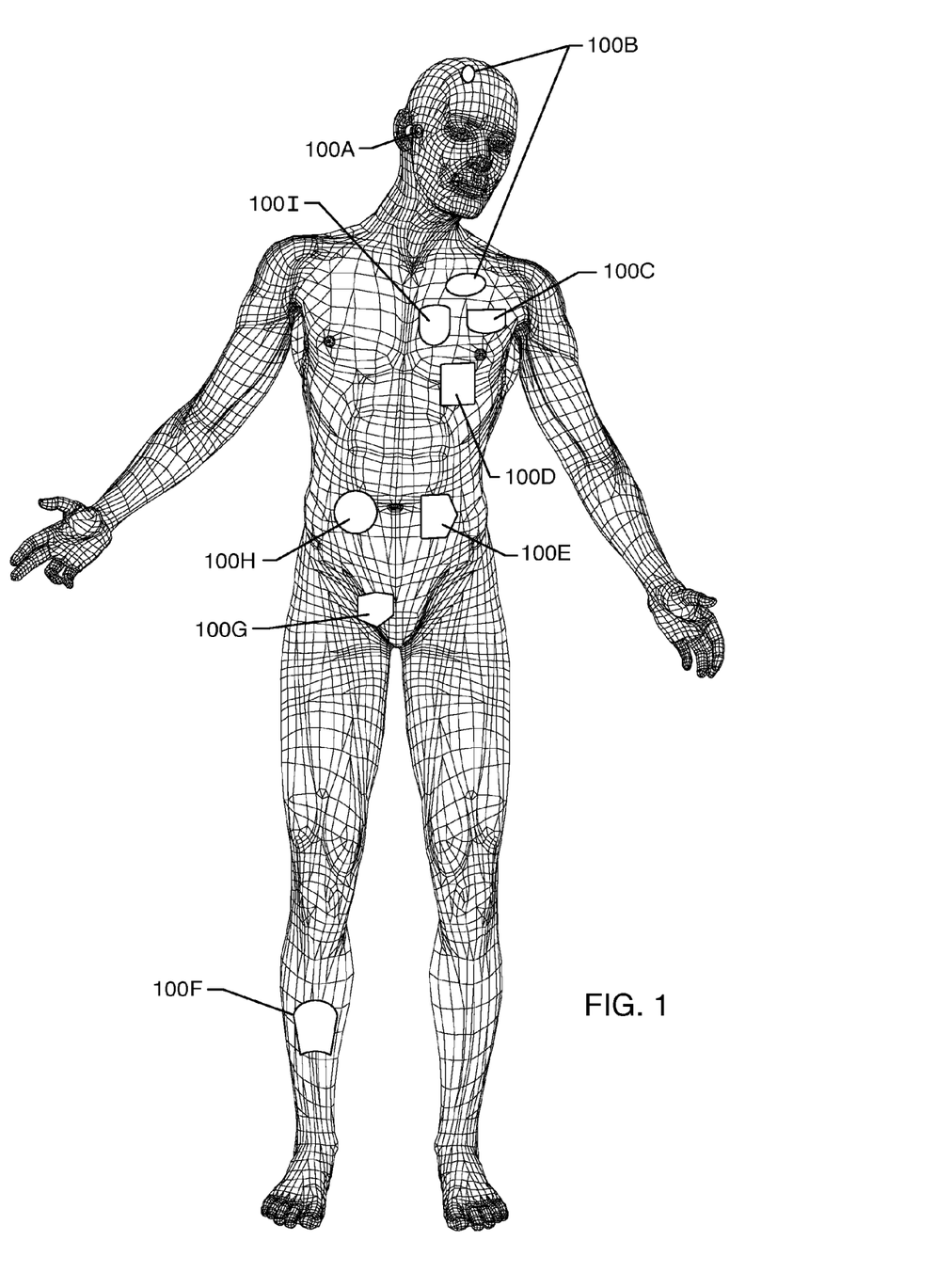
FIG. 1 is a wire-formed diagram of a generic human body illustrating placement of a number of implanted medical devices.

FIG. 1 is a wire formed diagram of a generic human body showing a number of implanted medical devices. 100A represents a family of hearing devices which can include the group of cochlear implants, piezoelectric sound bridge transducers and the like. 100B represent a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. The lead wires associated with a deep brain stimulator are often placed using real time MRI imaging. Most commonly such lead wires are placed during real time MRI. 100C shows a cardiac pacemaker which is well-known in the art. 100D includes the family of left ventricular assist devices (LVAD's), and artificial hearts. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of bone growth stimulators for rapid healing of fractures. 100G includes urinary incontinence devices. 100H includes the family of pain relief spinal cord stimulators and antitremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices.

Figure 2:
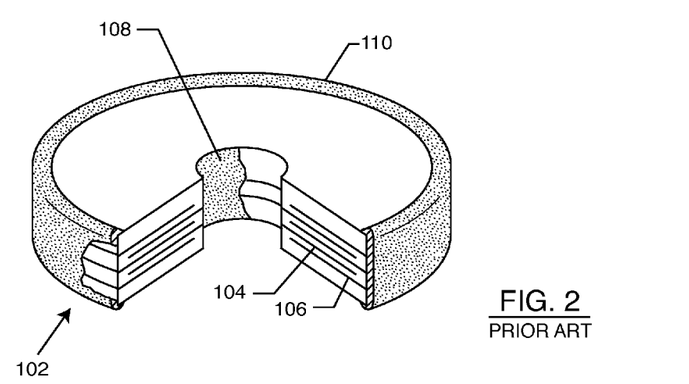
FIG. 2 is a partially fragmented perspective view of a prior art unipolar discoidal feedthrough capacitor.

FIG. 2 is a prior art unipolar discoidal feedthrough capacitor 102. The capacitor 102 includes an active internal electrode plate set 104, a ground electrode plate set 106, an inside diameter termination surface 108 which is connected electrically to the active electrode plate set 104, and an outside diameter termination surface 110 which is both solderable and electrically conductive, and is connected to the outside diameter (ground) electrode plate set 106.

Figures 3, 4:
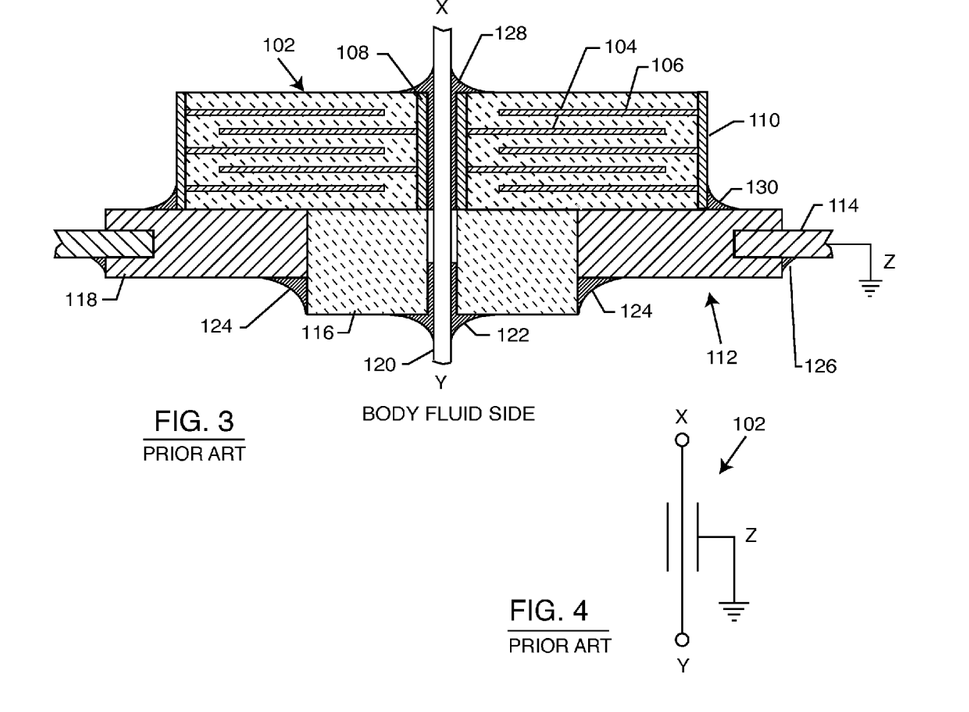
FIG. 3 is a cross-sectional view of the unipolar feedthrough capacitor of FIG. 2 shown mounted to a hermetic terminal of an active implantable medical device (AIMD)
FIG. 4 is an electrical schematic diagram of the feedthrough capacitor of FIGS. 2 and 3.

FIG. 3 is a cross-section of the unipolar feedthrough capacitor 102 of FIG. 2 shown mounted to a hermetic terminal 112 of an active implantable medical device (AIMD). The hermetic terminal 112 is attached to, typically, a titanium housing 114, for example, of a cardiac pacemaker. An insulator 116, like alumina ceramic or glass, is disposed within the ferrule 118 and forms a hermetic seal against body fluids. A continuous terminal pin or lead wire 120 extends through the hermetic terminal 112, passing through aligned passageways through the insulator 116 and the capacitor 102. A gold braze 122 forms a hermetic seal joint between the terminal pin 120 and the insulator 116. Another gold braze 124 forms a hermetic seal joint between the alumina insulator 116 and the titanium ferrule 118. A laser weld 126 provides a hermetic seal joint between the ferrule 118 and the active implantable medical device (AIMD) housing 114. The feedthrough capacitor 102 is shown surface mounted in accordance with U.S. Pat. No. 5,333,095, and has an electrical connection 128 between its inside diameter metallization 108 and hence the active electrode plate set 104, and lead wire 120. The electrical connection 128 may be of a biocompatible material but such is not required since it is insulated from body fluids. There is also an outside diameter electrical connection 130 which connects the capacitor's outside diameter metallization 110 and hence the ground electrodes 106, to the ferrule 118. Feedthrough capacitors are very efficient high frequency devices that have minimal series inductance. This allows them to operate as EMI low-pass filters over very broad frequency ranges.

FIG. 4 is an electrical schematic diagram of the unipolar feedthrough capacitor of FIGS. 2 and 3.

Figure 5:
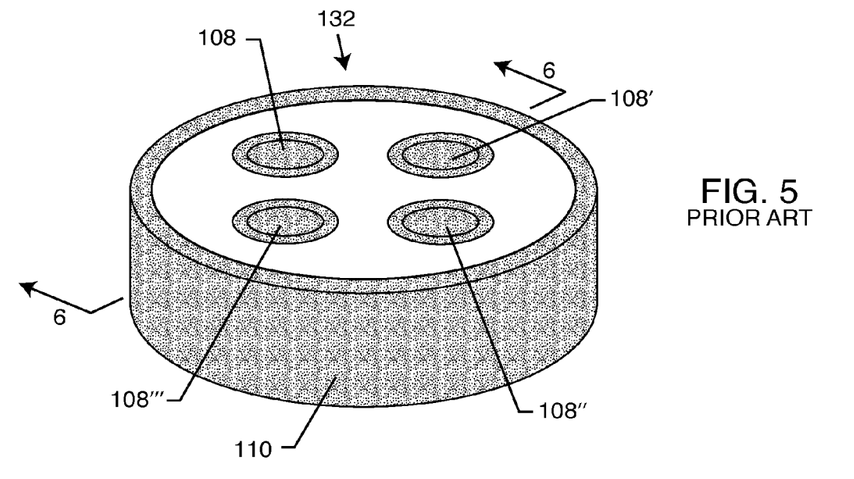
FIG. 5 is a perspective view of a prior art quadpolar feedthrough capacitor.

FIG. 5 is a prior art quadpolar feedthrough capacitor 132, which is similar in construction to that previously described in FIG. 2 except that it has four through holes.

Figure 6:
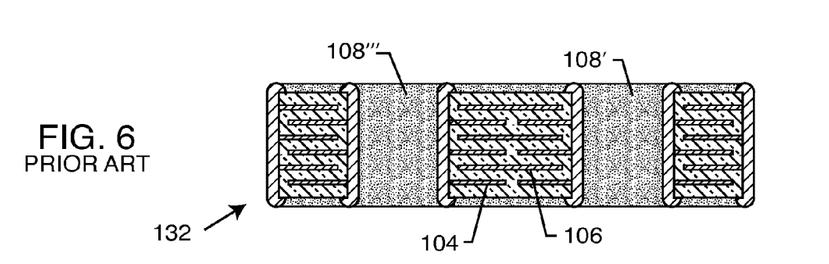
FIG. 6 is a sectional view taken generally along the line 6-6 of FIG. 5.

FIG. 6 is a cross-section showing the internal electrodes 104 and 106 of the quadpolar capacitor 132 of FIG. 5.

Figure 7:
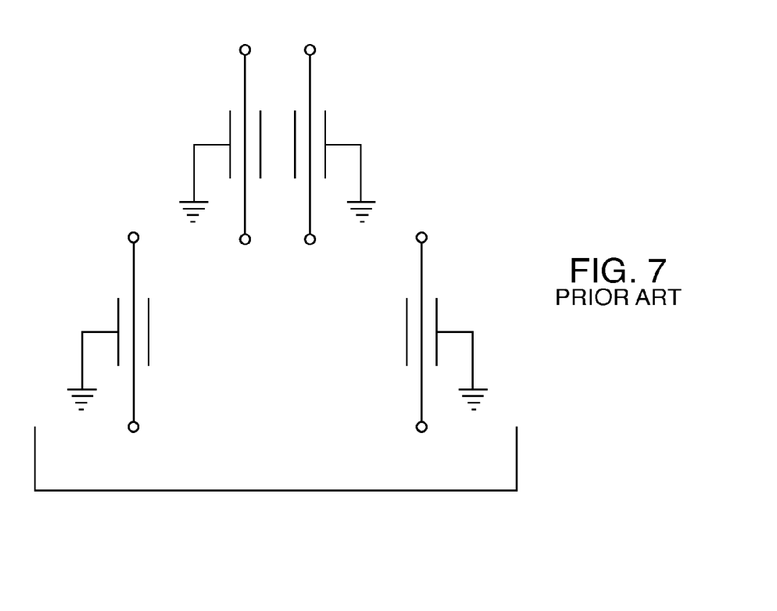
FIG. 7 is an electrical schematic diagram of the quadpolar feedthrough capacitor of FIGS. 5 and 6.

FIG. 7 is an electrical schematic diagram of the four feedthrough capacitors of the quadpolar feedthrough capacitor 132 of FIGS. 5 and 6.

Figure 8:
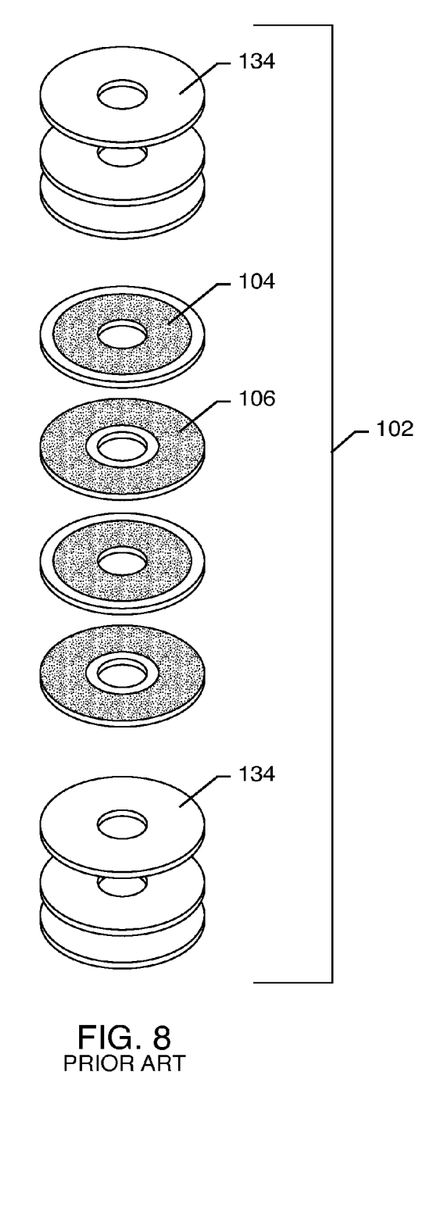
FIG. 8 is an exploded view of the unipolar feedthrough capacitor of FIGS. 2 and 3.

FIG. 8 is an exploded view showing the inner (active) and outer diameter (ground) electrodes of the unipolar feedthrough capacitor 102 of FIGS. 2 and 3. Here one can see the active electrode plate set 104 and the ground electrode plate set 106. Cover layers 134 are put on the top and bottom for added electrical insulation and mechanical strength.

Figure 9:
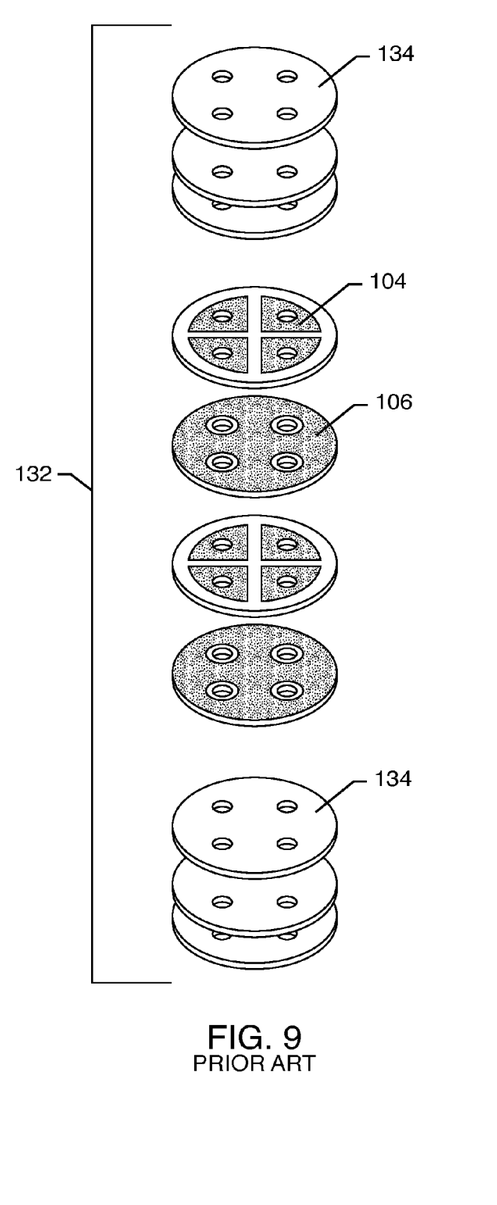
FIG. 9 is an exploded view similar to FIG. 8, but of the quadpolar feedthrough capacitor of FIGS. 5 and 6.

FIG. 9 is an exploded view of the prior art quadpolar feedthrough capacitor 132 illustrated in FIG. 5. The active electrode plate sets 104, the ground electrode plates sets 106, and the cover sheets 134 serve the same purposes as previously described.

As shown in FIGS. 2, 3, 5 and 6, prior art monolithic ceramic capacitors have been constructed with termination materials 108 and 110. Such termination materials cover both rectangular MLC chip capacitors and feedthrough chip capacitor through-hole passageway and outer diameter surfaces. The reasons for such termination metallization materials are: (1) to provide electrical connection to the active and ground electrode plates, which are set in parallel; and (2) to provide a surface wherein one can solder or otherwise make conductive attachments from the capacitor to other components in the circuitry. In the specific case of a human implant device, termination metallization materials 108 and 110 are utilized in the connection from the capacitor active electrode plates 104 to the terminal pin or lead wire 120, and the connection between the capacitor ground electrode plates 106 to the metallic ferrule 118.

Figure 10:
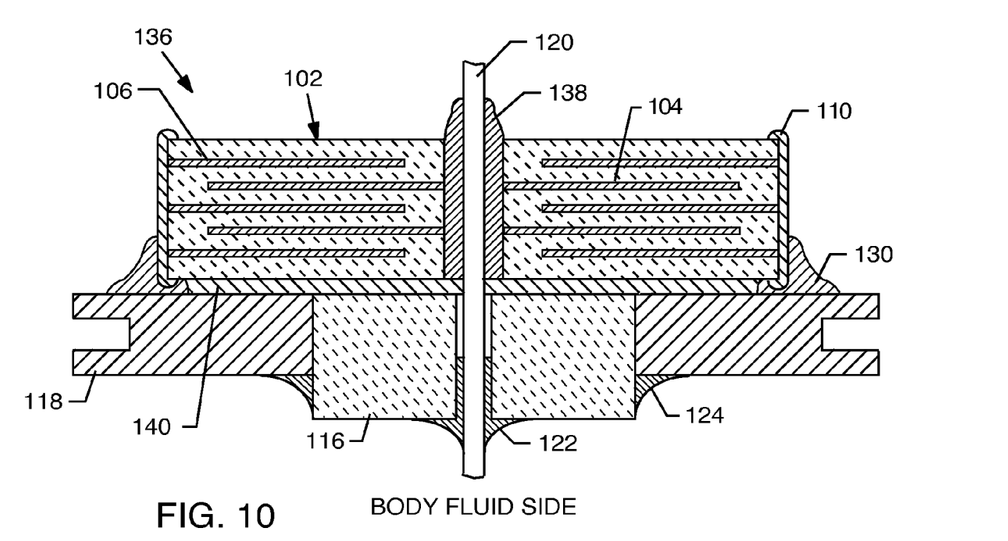
FIG. 10 is a cross-sectional view of a unipolar feedthrough terminal assembly similar to FIG. 3, wherein the inner metallization of the capacitor has been removed in accordance with the present invention.

The assembly 136 illustrated in FIG. 10 is similar to that illustrated in FIG. 3, except that the feedthrough capacitor 102 does not include an inner termination metallization surface (shown by the reference number 108 in FIG. 3). Instead, the lead wire or terminal pin 120 is conductively coupled to the set of active electrodes 104 of the capacitor 102 solely with an electrical connective material 138. The connective material 138 is not required to be biocompatible when used on a side of a capacitor that is disposed within the overall hermetic seal of the active implantable medical device. In this case, material 138 could be a typical silver flake or sphere-loaded conductive polyimide or epoxy, solder or the like. However, the conductive material 138 is preferably biocompatible and non-migratable if the assembly of FIG. 10 were reversed and the capacitor 102 were disposed on the body fluid side. In this case, biocompatible and non-migratable materials can be comprised of such materials as gold or platinum-filled thermal-setting conductive polyimide or any other conductive material that has been loaded with suitable particles such as gold or platinum such that it can make a direct electrical contact with the active electrode plates 104, as shown.

It is important that the conductive thermal-setting material 138 penetrate all the way down through the passageway of the feedthrough capacitor 102. This is best accomplished by injection or centrifuging. Accordingly, it is important that this material 138 not be allowed to extend underneath the capacitor 102 such that it could cause a short between the ferrule 118 or the outer metallization 110, which is still present in the embodiment illustrated in FIG. 10. Accordingly, an insulating material or insulating washer 140 is disposed below the capacitor 102 to prevent material 138 from migrating or penetrating into areas where it would be undesirable. In a preferred embodiment, the insulating material 140 is an adhesively coated polyimide washer.

When the capacitor 102 is disposed on the body fluid side, its active electrodes 104 are also preferably of a biocompatible and non-migratable material such as a noble metal including platinum or gold or an alternative alloy consisting of gold platinum and palladium. The thermal-setting conductive material 130 used to electrically connect the conductive ferrule 118 with the outer metallization 110 of the capacitor 102 is preferably comprised of non-migratable materials as described above. Of course, when the capacitor 102 is disposed within the hermetic seal of the overall AIMD, it is not required that its materials and electrodes be of biocompatible and non-migratable material.

Whereas the present invention is primarily directed to human implanted devices and applications, the embodiment illustrated in FIG. 10 has much broader application for all feedthrough capacitors whether they be for medical implant or not. The concept of making electrical connection from a lead wire 120 or to the outside diameter of the capacitor 102 without the need for termination materials (108 and 110) has advantages readily appreciated by those skilled in the art. It is very labor-intensive to apply these termination materials, which involve several process and termination firing steps. Eliminating the inner termination surface 108 and electrically coupling the lead wire 120 directly to the active electrode plates 104 with material 138 eliminates a number of time consuming and expensive process and cleaning steps relating to prior art capacitor inside diameter termination materials.

Figure 11:
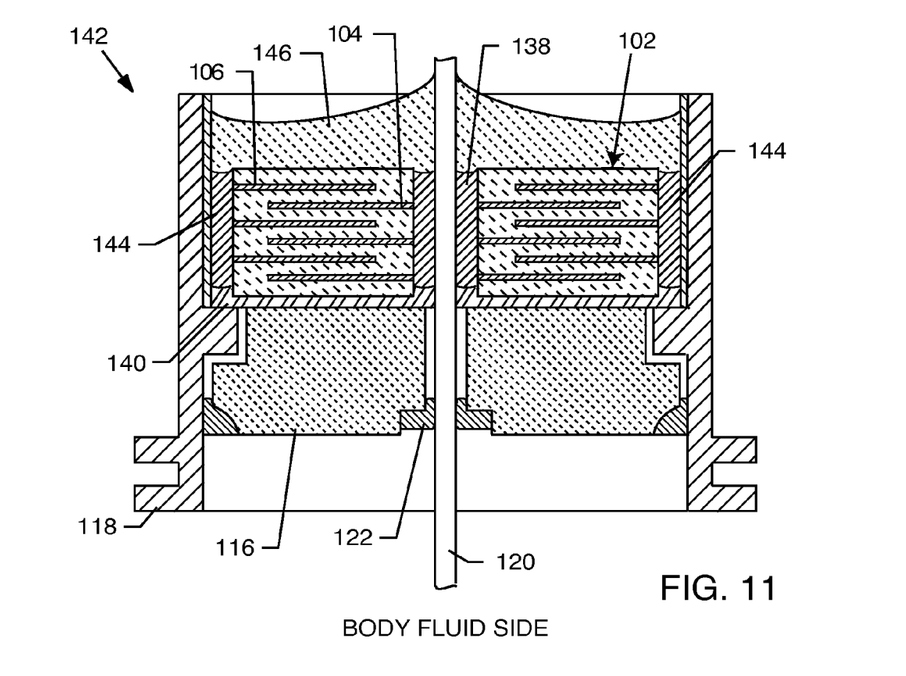
FIG. 11 is a cross-sectional view of another unipolar feedthrough terminal assembly, wherein the inner and outer metallization of the capacitor has been eliminated in accordance with the present invention.

FIG. 11 illustrates a terminal assembly 142 having a capacitor which is similar to that illustrated in FIG. 2. However, the unipolar feedthrough capacitor 102 embedded within the surrounding metallic ferrule 118 does not include inside diameter or outside diameter metallization (labeled with reference numbers 108 and 110 in FIG. 2). Instead, the feedthrough hole, which may be of any geometry, is filled with the conductive material 138 described above. Additionally, conductive material 144, which may comprise the same material as 138, directly conductively couples the ground electrode plates 106 to the hermetic terminal ferrule 118. Once again, insulative material, typically in the form of a washer 140, prevents shorting of the capacitor. The non-body fluid side of the capacitor within the ferrule 118 is covered with a non-conductive sealing epoxy 146 for cosmetic reasons and to protect the fragile ceramic material of the feedthrough capacitor.

Figure 12:
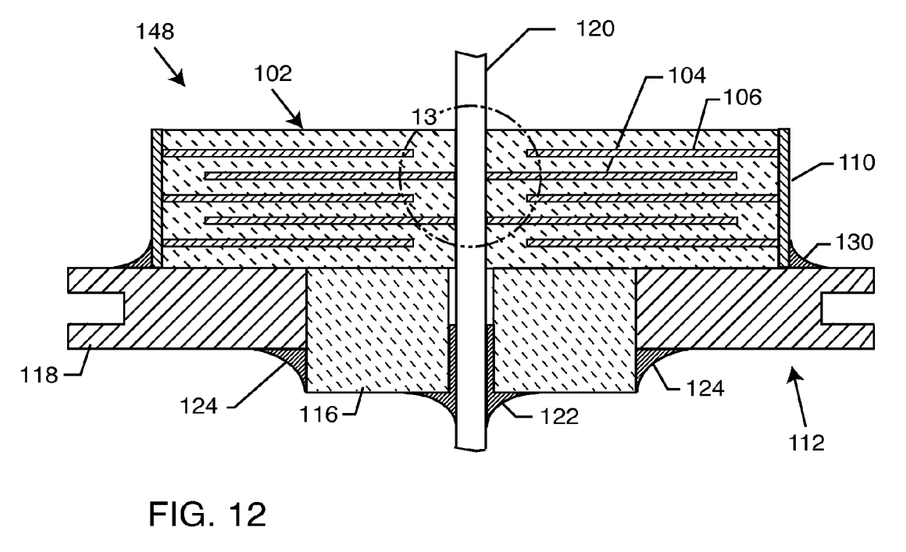
FIG. 12 is a cross-sectional view of another unipolar feedthrough terminal assembly similar to FIG. 10, wherein a terminal pin directly contacts the active electrode plates of the capacitor in accordance with the present invention.
Figure 13:
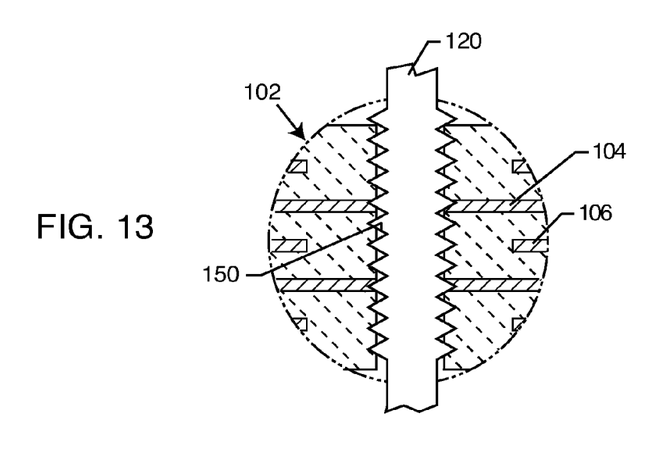
FIG. 13 is an enlarged sectional view taken generally from area "13" of FIG. 12, illustrating a knurled, threaded or roughened portion of the terminal pin designed to directly contact the active electrode plates.

With reference now to FIG. 12, yet another hermetic terminal assembly 148 is illustrated which shows an alternative method of electrically coupling a terminal pin or electrical lead 120 to the internal electrode set 104 of the capacitor 102. In this case, the pin or wire 120 is designed to form a very tight or pressed fit within the inside diameter or passageway of the capacitor 102. As illustrated in FIG. 13, the inner metallization 108 is absent such that the active electrode plates 104 directly contact the terminal pin or electrical lead wire 120 either through the enlargement of the terminal pin 120 or the reduction in diameter of the passageway through the capacitor 102. In a preferred embodiment, the electrical lead 120 has been prepared prior to inserting with a knurled, sputtered or roughened area 150 which coincides with the internal electrode set 104 to increase the electrical contact surface area directly to electrodes 104.

It will be appreciated that the embodiments illustrated in FIGS. 10-13 may incorporate the non-migratable materials previously discussed so as to have application in implantable biomedical devices in which the electronic network components of the EMI filter assembly, including the capacitor, are exposed to body fluid. The selection and use of the non-migratable materials and the construction of the capacitor, terminal pin or lead wire, and conductive connections provide a biocompatible surface which prevents dendritic growth and the like.

Figure 14:
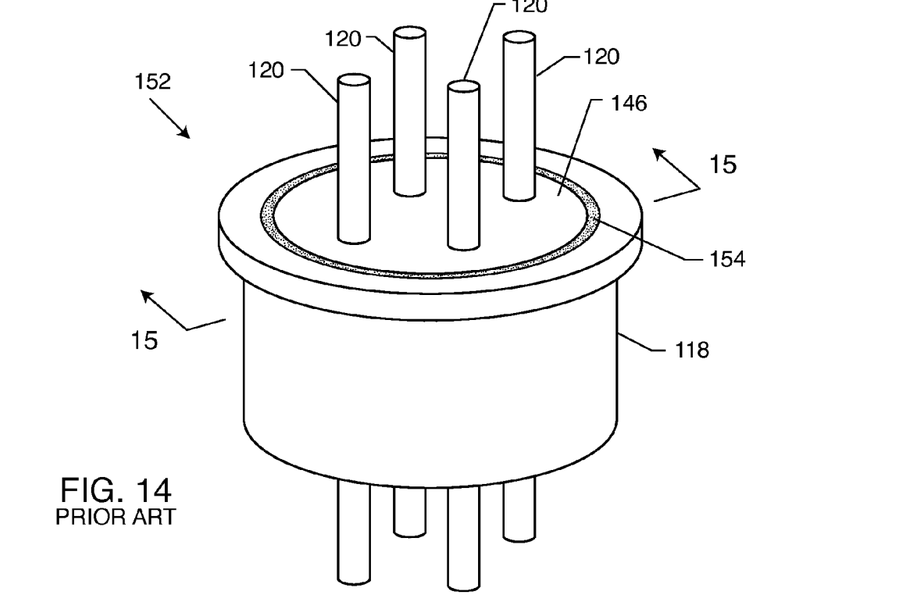
FIG. 14 is a perspective view of a prior art quadpolar feedthrough terminal assembly including the feedthrough capacitor of FIGS. 5 and 6.
Figure 15:
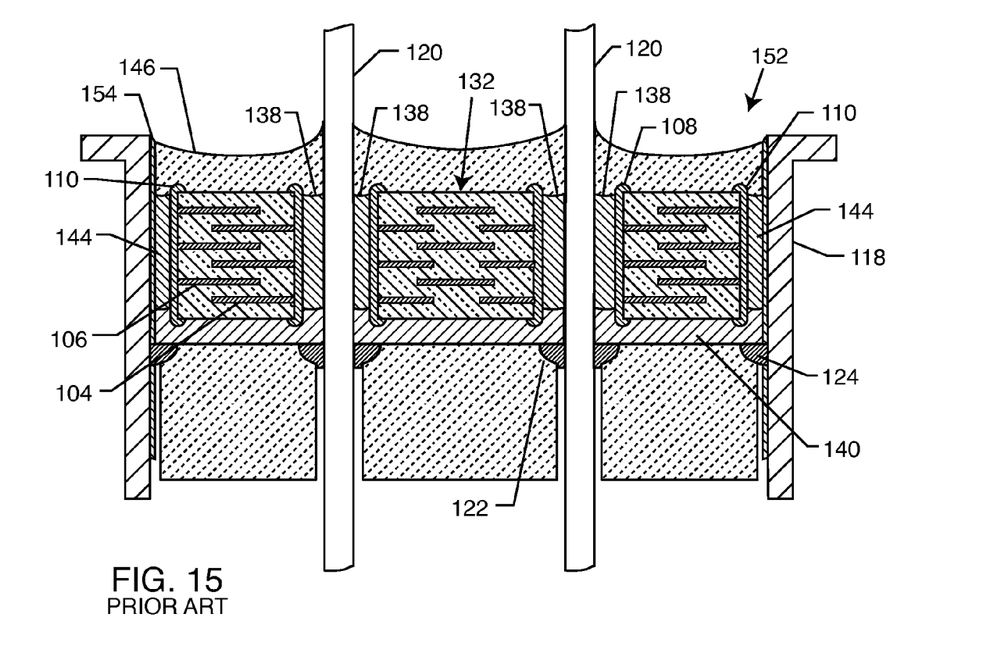
FIG. 15 is a sectional view taken generally along the line 15-15 from FIG. 14.

FIGS. 14 and 15 represent a prior art quadpolar feedthrough terminal assembly having 152 a capacitor 132 similar to that illustrated in FIGS. 5 and 6. The bottom surface of the capacitor 132 has been flooded with a nonconductive epoxy 140. As exemplified in U.S. Pat. No. 4,424,551, the insulative material 140 is cured so that the capacitor 132 is bonded into the case or ferrule 118. Subsequent to this, the entire surface above the capacitor 132 is flooded with conductive thermal-setting material 138, 144, which is then centrifuged into place. It is very important during the centrifuge operation that material not flow underneath the capacitor 132 thereby forming a short between the ferrule 118 and the capacitor inside diameter pins 120. An optional insulative epoxy coating 146 could be added to cosmetically cover the surface of the capacitor 132 and offer it some degree of mechanical protection. As can be seen in this prior art assembly, there is no way for the conductive thermal-setting 138 at the inside diameter to reach the gold braze 122. Also, it is not possible for the outside diameter conductive thermal-setting 144 to reach the gold braze 124. This type of prior art assembly is sensitive to any type of titanium oxide build-up that may occur on the inside diameter of the titanium ferrule. U.S. Pat. No. 6,765,779, which is incorporated herein by reference, shows and describes gold bond pads and techniques which allow the conductive polyimide or other material to reach the gold braze.

Notably, the capacitor 132 includes metalized inner termination surfaces 108 surrounding the inside passageways or through-holes, and an outside metalized termination surface surrounding the outer periphery of the capacitor 132. As mentioned previously, the inner termination surfaces conductively couple the active electrode plate sets 104 in parallel. Similarly, the outside termination surface 110 conductively couples the ground electrode plate set 106 in parallel. A thin conductive surface 154, such as gold or a gold alloy, may be sputtered, plated or the like onto the inside surface of the ferrule 118 to ensure a reliable electrical connection between the outside termination surface 110 of the capacitor 102 and the ferrule 118 through the conductive thermal-setting material 144. Similarly, the conductive thermal-setting material 138 provides a reliable electrical connection between the pins or lead wires 120 and the inner diameter termination surfaces 108 of the capacitor 132.

Figure 16:
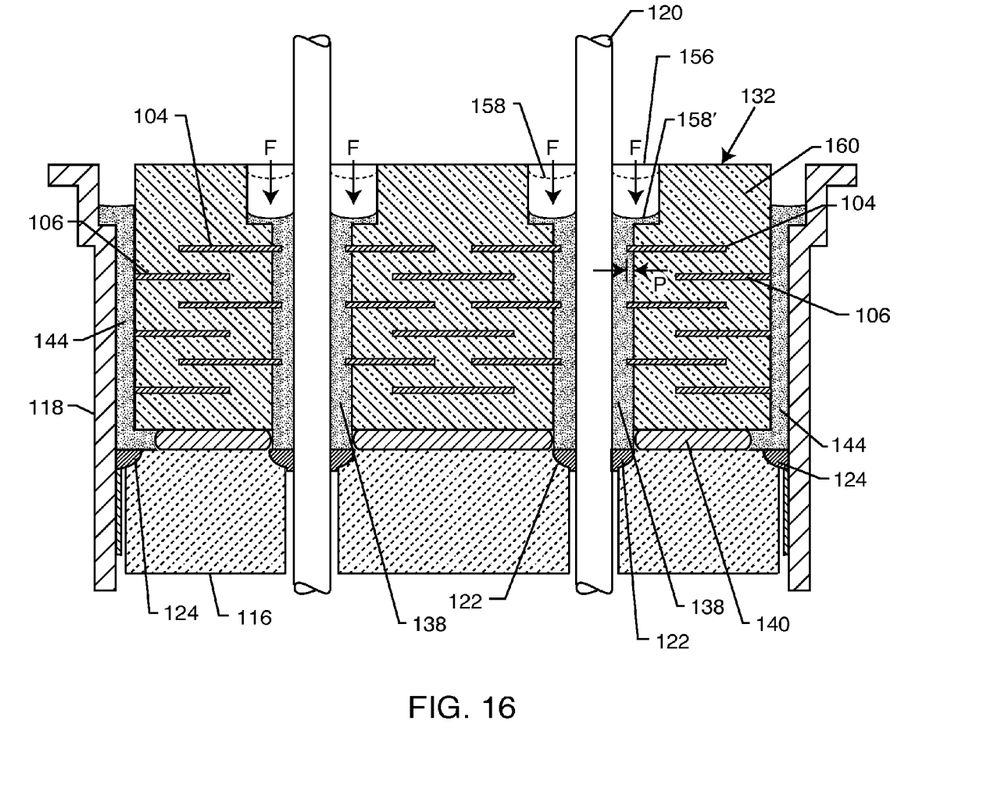
FIG. 16 is a sectional view similar to FIG. 15, except that the capacitor inside diameter metalization has been completely eliminated in accordance with the present invention.

FIG. 16 is very similar to FIG. 15 except that the capacitor inside diameter metallization (108) and the outside diameter or perimeter metallization (110) have been completely eliminated. There is also no need for metallization on the inside diameter of the well 156 formed on top of the capacitor 132. In FIG. 16, one can see that the active electrodes 104 make direct contact with a thermal-setting conductive polymer 138. A syringe or robotic dispenser is first used to dispense the thermal-setting polymer 138 into the well 156 to the approximate level of 158. Then during centrifuging, centrifugal forces F are applied to the material 138 so it settles down into location 158'. This has the effect of causing the material 138 to solidly pack into the area around the excursion of the electrode plates 104. As noted above, the outside diameter or perimeter metallization (110) has also been removed from capacitor 132. The thermal-setting conductive material 144 is first dispensed into a well around the outer circumference or perimeter of the capacitor 132. Centrifuging or equivalent operations are then used to drive material 144 into the annular space between the outside diameter of the capacitor 132 and the inside diameter of the ferrule 118. In accordance with U.S. Pat. No. 6,765,779, the thermal-setting material 144 should contact a gold braze material 124 directly. This precludes the formation of undesirable oxides which can harm the high frequency performance of the feedthrough capacitor filter.

Referring once again to the inside diameter, the contact between the thermal-setting conductive epoxy or polyimide electrical connection material 138 and the active electrode plate set 104, can be further improved by controlling the thermal shrinkage and the rheology between the bulk ceramic 160 and the electrode plates 104 themselves. This has the effect of causing the electrodes to protrude into the inner passageway by a distance P as shown. This can be done by variations in solvent and metal loading between the bulk dielectric 160, in its green state, and the electrode plates 104. First, the feedthrough capacitor through hole is drilled and then the ceramic capacitor is sintered (fired) at very high temperature. This makes it into a hard monolithic ceramic block. Having the bulk dielectric 160 shrink in a linear direction during sintering more than the electrode 104 causes the electrode 104 to protrude out into the inside diameter area. This protrusion space is noted as P. In this way, the electrically thermal-setting conductive material 138 makes contact not only at the end of the electrode plates 104, but also along the edges around the protruding part of the electrode thereby reducing the contact resistance and improving the reliability of the connection. The protruding part of the electrode P can be further enhanced by a process of acid-etching. With the right solution of acid, one can cause the barium titinate or dielectric material 160 to be selectively etched while leaving the electrode 104 intact. This has the effect of causing the electrode protrusion P into the capacitor through-hole space to be increased. It is also important that the conductive polyimide of the conductive thermal-setting material 138 also touch the appropriate gold braze 122 to prevent the formation of oxides.

Figure 17:
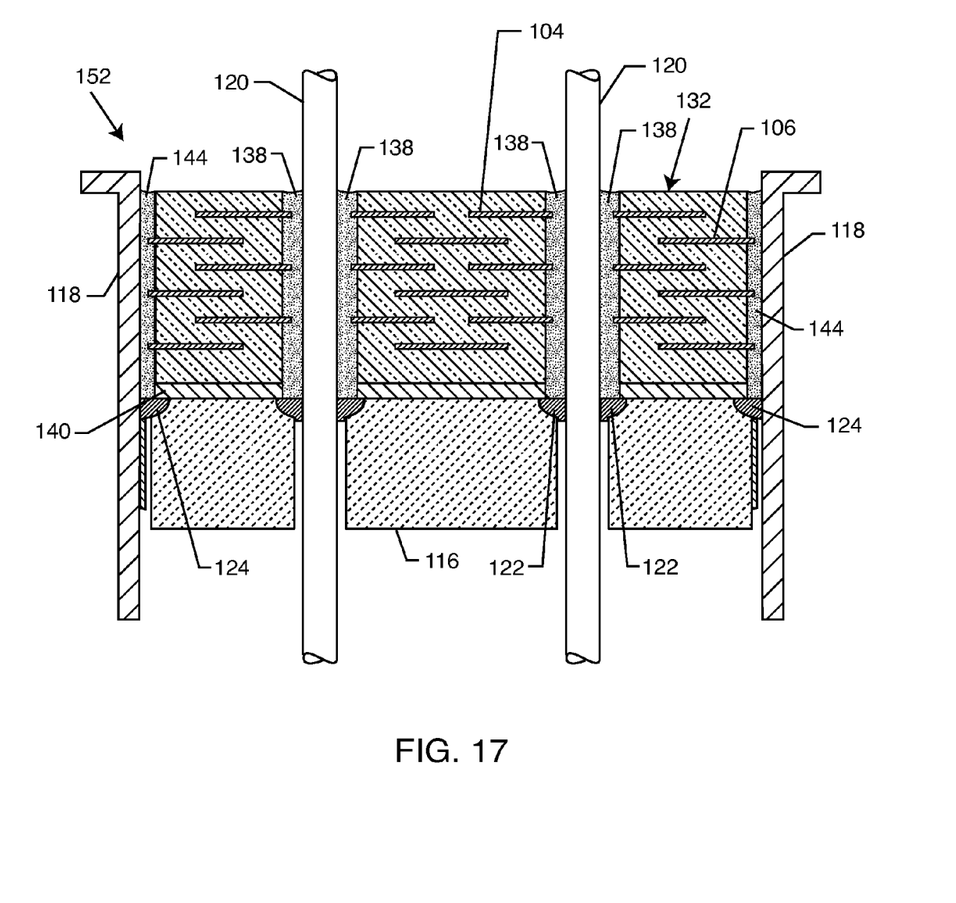
FIG. 17 is a sectional view similar to FIG. 15, except that the capacitor inside and outside diameter metalizations have both been completely eliminated in accordance with the present invention.

Elimination of the capacitor inside diameter termination (108) reduces a number of process steps and greatly reduces the cost of the overall assembly. In an alternative embodiment shown in FIG. 17, the outside diameter metallization (110) could also be eliminated and the ground electrode plates 106 could also protrude around the outside diameter of the capacitor 132. In this case, the outside diameter of the capacitor 132 would also be put into the well-like ferrule 118 and/or the thermal-setting conductive material 144 would have to be placed up along the side such that the ground electrode plates 106 all ended up electrically in parallel.

Although several embodiments of the invention have been described in detail for purposes of illustration, various modifications of each may be made without departing from the spirit and scope of the invention. Accordingly, the invention is not to be limited, except as by the appended claims.

What is claimed is:

1. An electromagnetic interference (EMI) filter, comprising:
a capacitor comprised of a dielectric body having at least one first electrode plate and at least one second electrode plates disposed therein, at least one of the first or second electrode plates having an edge exposed at a surface of the dielectric body; and
a conductive lead and/or a conductive ferrule disposed adjacent to the exposed edge of the electrode plate and conductively coupled to the exposed edge of the electrode plates without an intervening conductive termination surface.

2. The EMI filter of claim 1, including an electrically conductive material disposed between the conductive lead and/or ferrule and the adjacent exposed edge of the electrode plate or plates, for directly conductively coupling the conductive lead and/or ferrule to the adjacent exposed edge of the electrode plate or plates.

3. The EMI filter of claim 2, wherein the exposed edge of the electrode plate or plates extends outwardly from the surface of the dielectric body.

4. The EMI filter of claim 3, wherein shrinkage of the dielectric body of the capacitor is greater than shrinkage of the electrode plate or plates during manufacture of the capacitor.

5. The EMI filter of claim 2, wherein the electrically conductive material comprises an adhesive.

6. The EMI filter of claim 5, wherein the adhesive comprises a thermal-setting adhesive.

7. The EMI filter of claim 6, wherein the thermal-setting adhesive includes a non-migratable and biocompatible conductive filler selected from the group consisting of titanium, platinum and platinum/iridium alloys, tantalum, niobium, zirconium, hafnium, nitinol, Co—Cr—Ni alloys such as MP35N, Havar® and Elgiloy®, stainless steel, gold, ZrC, ZrN, TiN, NbO, TiC, TaC, Indium Oxide/Indium Tin Oxide.

8. The EMI filter of claim 5, wherein the adhesive comprises a polymer selected from the group consisting of: epoxies, polyimides, polyethylene oxide, polyurethane, silicone, polyesters, polycarbonate, polyethylene, polyvinyl chloride, polypropylene, methylacrylate, para-xylylene, and polypyrrhol.

9. The EMI filter of claim 5, wherein the adhesive includes a conductive metal filler.

10. The EMI filter of claim 9, wherein the metal filler comprises a biocompatible or noble metal filler.

11. The EMI filter of claim 1, wherein the surface of the dielectric body of the capacitor comprises an acid-etched surface.

12. The EMI filter of claim 1, wherein the conductive lead and/or ferrule directly contacts the exposed edge of the electrode plate or plates.

13. The EMI filter of claim 12, wherein a surface of the conductive lead and/or ferrule comprises a knurled, sputtered, threaded or roughened surface.

14. The EMI filter of claim 1, wherein the capacitor and the conductive lead and/or ferrule comprise bio-compatible and non-migratable materials suitable for prolonged direct body fluid exposure.

15. The EMI filter of claim 1, wherein the capacitor comprises a feedthrough capacitor having at least one through-hole in which at least a portion of the conductive lead is disposed, and an outer-periphery adjacent, at least in part, to the conductive ferrule.

16. The EMI filter of claim 15, wherein the at least one first electrode plate has an edge exposed at an inner surface of the through-hole, and the conductive lead is conductively coupled to the exposed edge of the at least one first electrode plate without an intervening conductive termination surface fixed to the inner surface of the through-hole over the exposed edge of the at least one first electrode plate.

17. The EMI filter of claim 15 or 16, wherein the at least one electrode plate has an edge exposed at the outer periphery of the capacitor, and the conductive ferrule is conductively coupled to the exposed edge of the at least one second electrode plate without an intervening conductive termination surface fixed to the outer periphery of the capacitor over the exposed edge of the at least one second electrode plate.

18. A process of manufacturing an electromagnetic interference (EMI) filter, comprising the steps of:
providing a capacitor comprised of a dielectric body having at least one first electrode plate and at least one second electrode plate therein, at least one of the electrode plates having an edge exposed at a surface of the dielectric body;
placing a conductive lead and/or a ferrule adjacent to the exposed edge of the electrode plate or plates; and
conductively coupling the exposed edge of the electrode plate or plates directly to the conductive lead and/or ferrule without an intervening conductive termination surface.

19. The process of claim 18, including the steps of:
providing a capacitor comprised of a dielectric material having active and ground electrode plates therein, and at least one through-hole;
forming a well in a surface of the capacitor at one end of the through-hole;
inserting a pin or a lead wire at least partially into the through-hole;
placing an electrically conductive material in the well, wherein the electrically conductive material comprises a liquid or semi-liquid material during at least a portion of the manufacturing process; and
utilizing the electrically conductive material to conductively couple the pin or the lead wire to at least one of the electrode plates.

20. The process of claim 19, wherein the electrically conductive material conductively couples the lead to at least one of the electrode plates directly and without an intervening connective termination surface for the electrode plate or plates.

21. The process of claim 20, wherein shrinkage of the dielectric material of the capacitor is greater than shrinkage of the electrode plates such that an end of the electrode plate or plates is conductively coupled to the electrically conductive material, which extends inwardly from the dielectric material into the through-hole.

22. The process of claim 20, including the step of acid-etching the dielectric material adjoining the through-hole prior to the step of utilizing the electrically conductive material to conductively couple the pin or the lead wire to at least one of the electrode plates.

* * * * *

UNITED STATES PATENT AND TRADEMARK OFFICE
CERTIFICATE OF CORRECTION

PATENT NO. : 8,179,658 B2  Page 1 of 1
APPLICATION NO. : 12/563919
DATED : May 15, 2012
INVENTOR(S) : Brendel et al.

It is certified that error appears in the above-identified patent and that said Letters Patent is hereby corrected as shown below:

Column 10, line 51 delete "plates" and insert --plate--

Column 10, line 57 delete "plates" and insert --plate--

Signed and Sealed this
Twenty-third Day of October, 2012

David J. Kappos
*Director of the United States Patent and Trademark Office*